United States Patent [19]

Sugiyama et al.

[11] Patent Number: 5,470,759
[45] Date of Patent: Nov. 28, 1995

[54] ANTI-GLYCATED HEMOGLOBIN MONOCLONAL ANTIBODY AND METHOD FOR MEASURING GLYCATED HEMOGLOBIN

[75] Inventors: Masami Sugiyama; Yoshiaki Uchida; Yoshihiro Kurano; Aiko Tanaka; Tetsuji Tanimoto, all of Tokyo, Japan

[73] Assignee: Fujirebio, Inc., Tokyo, Japan

[21] Appl. No.: 73,340

[22] Filed: Jun. 7, 1993

[30] Foreign Application Priority Data

Jun. 10, 1992 [JP] Japan .................................. 4-177444
Jun. 16, 1992 [JP] Japan .................................. 4-181708

[51] Int. Cl.$^6$ .......................... G01N 33/538; G01N 33/72
[52] U.S. Cl. .......................... 436/541; 436/533; 436/66; 435/7.21; 435/14; 530/388.25
[58] Field of Search .................. 435/7.9, 7.92, 435/7.94, 14, 7.21; 436/533, 534, 811, 66, 67, 541, 66; 530/388.25

[56] References Cited

U.S. PATENT DOCUMENTS

| | | | |
|---|---|---|---|
| 4,647,654 | 3/1987 | Knowles | 530/326 |
| 4,658,022 | 4/1987 | Knowles et al. | |
| 4,727,036 | 2/1988 | Knowles et al. | |
| 4,847,209 | 7/1989 | Lewis et al. | 436/533 |
| 4,861,728 | 8/1989 | Wagner | 436/381 |

FOREIGN PATENT DOCUMENTS

| | | |
|---|---|---|
| 0201187A1 | 11/1986 | European Pat. Off. |
| 0329994A1 | 8/1989 | European Pat. Off. |

OTHER PUBLICATIONS

Winocour, P. H., et al., Ann. Clin. Biochem., vol. 24 (Pt. 1), pp. 47–52, Jan. 1987.

*Primary Examiner*—Toni R. Scheiner
*Assistant Examiner*—Nancy J. Parsons
*Attorney, Agent, or Firm*—Cooper & Dunham

[57] ABSTRACT

A method for measuring glycated hemoglobin is disclosed, which comprises contacting a sample with an anti-hemoglobin antibody being bound to a solid phase, adding thereto an anti-glycated hemoglobin antibody, and then measuring the anti-glycated hemoglobin antibody bound to the solid phase via glycated hemoglobin and the anti-hemoglobin antibody. A method for measuring glycated hemoglobin is further disclosed, which comprises mixing a sample with particles on which an anti-glycated hemoglobin antibody is bound to cause immunoagglutination reaction. A method for measuring glycated hemoglobin is furthermore disclosed, which comprises mixing a sample with a solution containing a monoclonal antibody specific for glycated hemoglobin, and then measuring the change in the turbidity of the resulting mixture. A method is disclosed for measuring glycated hemoglobin which comprises mixing a sample with unsensitized latex particles and an anti-glycated hemoglobin antibody, to cause immunoagglutination reaction. There is disclosed a method for measuring glycated hemoglobin which comprises mixing a sample with unsensitized latex particles and particles on which an anti-glycated hemoglobin antibody is bound, to cause immunoagglutination reaction. Still furthermore, an anti-glycated hemoglobin monoclonal antibody having a high specificity for human glycated hemoglobin is disclosed.

2 Claims, 2 Drawing Sheets

ANTI-GLYCATED HEMOGLOBIN MONOCLONAL ANTIBODY AND METHOD FOR MEASURING GLYCATED HEMOGLOBIN

FIELD OF THE INVENTION

This invention relates to a method for measuring glycated hemoglobin.

BACKGROUND OF THE INVENTION

Since it has been known that the concentration of glycated hemoglobin ($A_{1c}$) in blood increases in the case of diabetic patients, measurement of glycated hemoglobin is used for the diagnosis of diabetes and examination of the progress of the disease, together with the measurement of blood sugar level.

In the prior art method, measurement of glycated hemoglobin is carried out by binding glycated hemoglobin in a sample (erythrocyte extract) directly to a solid phase, washing the solid phase, allowing the bound hemoglobin to react with a labeled anti-glycated hemoglobin antibody, washing the solid phase again and then measuring levels of the label. This method, however, requires a time-consuming pretreatment for the direct binding of glycated hemoglobin in each sample to the solid phase (for example, an overnight incubation at 4° C.), thus rendering quick measurement of a large number of samples impossible.

In view of the above, it therefore becomes an object of the present invention to provide a method for the simple and quick measurement of glycated hemoglobin.

SUMMARY OF THE INVENTION

The inventors of the present invention have conducted intensive studies and found that the time-consuming step involved in the prior art method, namely a step for the binding of glycated hemoglobin in each sample to a solid phase, can be eliminated and therefore glycated hemoglobin can be measured quickly, when an anti-hemoglobin antibody bound to a solid phase in advance is allowed to react with a sample and the reaction product is subsequently allowed to react with an anti-glycated hemoglobin antibody. The present invention has been accomplished on the basis this finding.

Particularly, in accordance with the present invention, there is provided a method for measuring glycated hemoglobin which comprises contacting a sample with an anti-hemoglobin antibody being bound to a solid phase, adding thereto an anti-glycated hemoglobin antibody, and then measuring the anti-glycated hemoglobin antibody bound to the solid phase via glycated hemoglobin and the anti-hemoglobin antibody. (This embodiment will be referred to as "the first embodiment" according to the present invention.)

The present inventors have further found that glycated hemoglobin can be measured by binding an anti-hemoglobin antibody to particles, mixing the particles with a sample to form agglutinations, and then measuring glycated hemoglobin based on the agglutinations.

Namely, according to the present invention, there is further provided a method for measuring glycated hemoglobin which comprises mixing a sample with particles on which an anti-glycated hemoglobin antibody is bound to cause immunoagglutination reaction, and then measuring agglutinations formed by the immunoagglutination reaction. (This embodiment will be referred to as "the second embodiment" according to the present invention.)

The present inventors have furthermore found that glycated hemoglobin can be measured by mixing a solution containing a monoclonal antibody specific for human glycated hemoglobin with a sample, and then measuring glycated hemoglobin based on the change of the turbidity of the resulting mixture.

Namely, according to the present invention, there is furthermore provided a method for measuring glycated hemoglobin which comprises mixing a sample with a solution containing a monoclonal antibody specific for glycated hemoglobin, and then measuring the change in the turbidity of the resulting mixture. (This embodiment will be referred to as "the third embodiment" according to the present invention.)

The inventors of the present invention have still conducted intensive studies and found that the time-consuming step involved in the prior art method can be eliminated and therefore glycated hemoglobin can be measured quickly, when a sample is mixed with unsensitized latex particles and an anti-glycated hemoglobin antibody, or with unsensitized latex particles and then with an anti-glycated hemoglobin antibody.

Namely, according to the present invention, there is still provided a method for measuring glycated hemoglobin which comprises mixing a sample with unsensitized latex particles and an anti-glycated hemoglobin antibody, or with unsensitized latex particles and subsequently with an anti-glycated hemoglobin antibody, to cause immunoagglutination reaction, and then measuring agglutinations formed by the immunoagglutination reaction. (This embodiment will be referred to as "the fourth embodiment" according to the present invention.)

The present inventors have still further found that glycated hemoglobin can be measured by mixing a sample with unsensitized latex particles and particles on which an anti-glycated hemoglobin antibody is bound, or with unsensitized latex particles and subsequently with particles on which an anti-glycated hemoglobin antibody is bound, to form agglutinations, and then measuring the agglutinations.

Namely, according to the present invention, there is still further provided a method for measuring glycated hemoglobin which comprises mixing a sample with unsensitized latex particles and particles on which an anti-glycated hemoglobin antibody is bound, or with unsensitized latex particles and subsequently with particles on which an anti-glycated hemoglobin antibody is bound, and then measuring agglutinations formed by the immunoagglutination reaction. (This embodiment will be referred to as "the fifth embodiment" according to the present invention.)

Still furthermore, according to the present invention, there is provided an anti-glycated hemoglobin monoclonal antibody having a high specificity foe glycated hemoglobin.

Other objects and advantages of the present invention will be made apparent as the description progresses.

DETAILED DESCRIPTION OF THE INVENTION

Figure 1:
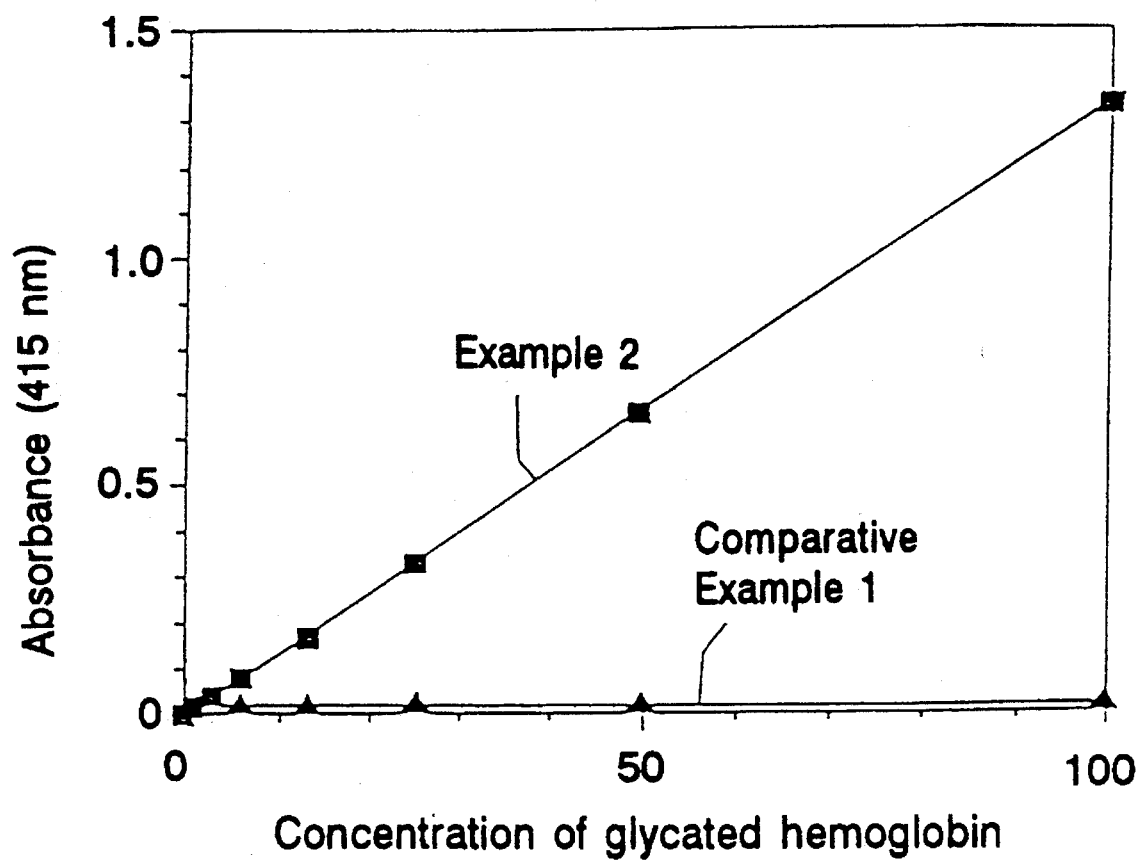
FIG. 1 is a graph showing effects of the anti-human glycated hemoglobin monoclonal antibody prepared in Example 1 and a commercially available anti-human glycated hemoglobin antibody (Chemicon International Inc. (U.S.A.)) on the measurement of samples containing human glycated hemoglobin at various concentrations.

The present invention is described below in further detail.

According to the first embodiment of the present invention, there is provided a method for measuring glycated hemoglobin which comprises contacting a sample, which contains or does not contain glycated hemoglobin, with an anti-hemoglobin antibody being bound to a solid phase to react the glycated hemoglobin with the anti-hemoglobin antibody, adding thereto an anti-glycated hemoglobin antibody to react the anti-glycated hemoglobin antibody with the glycated hemoglobin, and then measuring the anti-glycated hemoglobin antibody being bound to the solid phase via the glycated hemoglobin and the anti-hemoglobin antibody.

According to the first embodiment of the present invention, when a large quantity of a solid phase material to which an anti-hemoglobin antibody is bound is prepared in advance, glycated hemoglobin in a sample can be bound to the solid phase via the anti-hemoglobin antibody in each measurement, by allowing the sample and the anti-hemoglobin antibody being bound to the solid phase to undergo antigen-antibody reaction. In comparison with the prior art process in which glycated hemoglobin is directly bound to a solid phase, this method can be completed within a considerably shortened period of time by a factor of $1/10$ or less.

According to the second embodiment of the present invention, there is provided a method for measuring glycated hemoglobin which comprises mixing a sample, which contains or does not contain glycated hemoglobin, with particles on which an anti-glycated hemoglobin antibody is bound to cause immunoagglutination reaction of the glycated hemoglobin with the anti-glycated hemoglobin antibody, and then determining the glycated hemoglobin based on agglutinations formed by the immunoagglutination reaction.

Also, according to the third embodiment of the present invention, there is provided a method for measuring glycated hemoglobin which comprises mixing a solution containing a monoclonal antibody specific for human glycated hemoglobin with a sample, which contains or does not contain human glycated hemoglobin, and then determining the glycated hemoglobin based on the change in the turbidity of the resulting mixture.

The methods according to the second and third embodiments of the present invention, in which agglutination of particles and change in the turbidity of the mixture are respectively used as a mean for detecting glycated hemoglobin, also can measure glycated hemoglobin within a markedly shorter period of time in comparison with the prior art method.

According to the fourth embodiment of the present invention, there is provided a method for measuring glycated hemoglobin which comprises mixing a sample, which contains or does not contain glycated hemoglobin, with unsensitized latex particles and an anti-glycated hemoglobin antibody, or with unsensitized latex particles and subsequently with an anti-glycated hemoglobin antibody, to cause an immunoagglutination reaction of the anti-glycated hemoglobin antibody with the glycated hemoglobin being bound to the unsensitized latex particles, and then determining the glycated hemoglobin based on agglutinations formed by the immunoagglutination reaction.

According to the fourth embodiment of the present invention, glycated hemoglobin in a sample easily bind to unsensitized latex particles and, therefore, agglutination can be effected by simply reacting the glycated hemoglobin being bound to the unsensitized latex particle with an anti-glycated hemoglobin antibody, Because of this, binding of glycated hemoglobin in a sample to the unsensitized latex particles, antigen-antibody reaction with an anti-glycated hemoglobin antibody and subsequent agglutination can be effected in each measurement by simply mixing the sample, the anti-glycated hemoglobin antibody and the unsensitized latex particle. In comparison with the prior art process in which hemoglobin is directly bound to a solid phase, this method can be completed within a considerably shortened period of time by a factor of $1/10$ to $1/100$.

According to the fifth embodiment of the present invention, there is provided a method for measuring glycated hemoglobin which comprises mixing a sample, which contains or does not contains glycated hemoglobin, with unsensitized latex particles and particles on which an anti-glycated hemoglobin antibody is bound, or with unsensitized latex particles and subsequently with particles on which an anti-glycated hemoglobin antibody is bound, to cause an immunoagglutination reaction, and then determining the glycated hemoglobin based on agglutinations formed by the immunoagglutination reaction.

The method according to the fifth embodiment of the present invention also can measure glycated hemoglobin within markedly shorter period of time in comparison with the prior art method.

The solid phase to be used in the method of the first embodiment of the present invention may be any of those used in conventional art immunoassays. For example, wells of a plastic plate may preferably be used.

The anti-hemoglobin antibody is well known in the art, which may be either a polyclonal antibody or a monoclonal antibody. Binding of the anti-hemoglobin antibody to a solid phase may be effected by adding a solution of the antibody having a concentration of about 1 µg/ml to the solid phase and allowing the resulting solid phase to stand an overnight at 4° C. After the binding treatment, blocking with a protein such as BSA (bovine, serum albumin) is carried out in the usual way in order to block non-specific protein adsorption sites. When human glycated hemoglobin is measured, it is preferred to bind an anti-human hemoglobin antibody to the solid phase.

Next, the anti-hemoglobin antibody thus bound to the solid phase is allowed to contact with a sample to effect binding of glycated hemoglobin in the sample to the solid phase via the solid phase-bound anti-hemoglobin antibody by antigen-antibody reaction. The sample may be either erythrocyte extracts or total blood. The antigen-antibody reaction may be carried out, for example, at room temperature for about 2 hours.

After washing, the glycated hemoglobin bound to the solid phase via the anti-hemoglobin antibody is allowed to undergo antigen-antibody reaction with an anti-glycated hemoglobin antibody. The anti-glycated hemoglobin antibody may be either a polyclonal antibody or a monoclonal antibody, but preferably a monoclonal antibody form the viewpoint of high measuring accuracy. The present inventors have succeeded in preparing a monoclonal antibody which is capable of undergoing specific reaction with glycated hemoglobin but not substantially with normal hemoglobin (monoclonal antibody 3F10; a hybridoma capable of producing monoclonal antibody 3F10 has been deposited on Jun. 10, 1992 at National Institute of Bioscience and Human-Technology, Agency of Industrial Science and Technology, Ministry of International Trade and Industry of Japan, 1–3, Higashi 1-chome, Tsukubashi, Ibaraki, 305 Japan under accession No. FERM P-12998 (FERM BP-4311 under the Budapest Treaty), in accordance with a procedure which will be described later in detail in Example. This monoclonal antibody may be used preferably in the methods of the present invention. The antigen-antibody reaction of this case may be carried out under the same conditions as described above.

After subsequent washing, the anti-glycated hemoglobin antibody thus bound to the solid phase via the glycated hemoglobin and the anti-hemoglobin antibody is measured in accordance with various prior art techniques known in the field of immunoassays. For example, the measurement may be effected by labeling the anti-glycated hemoglobin antibody with an enzyme, a fluorescence dye, a radioactive material or the like and then measuring the label. It may be effected also by binding biotin to the anti-glycated hemoglobin antibody, allowing the bound biotin to react with labeled avidin and then measuring the label. The measurement may also be effected by allowing the anti-glycated hemoglobin antibody to react with a labeled antibody which can undergo specific reaction with the anti-glycated hemoglobin antibody and then measuring the label.

Preferred examples of the particles to be used in the method according to the second embodiment of the present invention, and in the method according to the fifth embodiment of the present invention, include latex particles having a particle size of from 0.05 to 5 μm, gelatin particles having a particle size of from 0.5 to 10 μm and animal erythrocytes.

Specific examples of the latex include styrene polymers, styrene-acrylic acid copolymers, styrene-butadiene copolymers, styrene-divinylbenzene copolymers. Specific examples of the gelatin particles include ones disclosed in U.S. Pat. No. 4,416,813 hereby incorporated by reference. Specific examples of the animal erythrocytes include ones obtained from animals such as fowls, ducks, goats, sheep, cattle and horses.

Methods for binding the antibody to the particles are well known in the art and, as will be described later in detail in Examples, it can easily be effected by dispersing the particles in an antibody solution, for example.

In the second embodiment of the present invention, the anti-glycated hemoglobin antibody may be bound to the particles as a single antibody source, but preferably in combination with the anti-hemoglobin antibody in order to obtain a strong agglutination image by their reaction with the antigen. In that case, it is preferred that the anti-glycated hemoglobin antibody and the anti-hemoglobin antibody are bound to the particles at a molar ratio of about 1:1. In this regard, it is necessary to select and employ an anti-hemoglobin antibody which does not cause by itself agglutination of hemoglobin.

When only the anti-glycated hemoglobin antibody is being bound to the particles, glycated hemoglobin in a sample can be detected by mixing the sample with the particles on, for example, a black slide glass and then observing the presence of agglutinated and precipitated particles. The glycated hemoglobin can also be quantitatively determined by an absorption measurement. When both of the anti-glycated hemoglobin antibody and the anti-hemoglobin antibody are bound to the particles, a strong agglutination image is also formed if the sample contains the glycated hemoglobin antibody, thus rendering possible detection of the glycated hemoglobin in the sample by observing the agglutination image with the naked eye.

Also in the second embodiment of the present invention, it is preferable to use the high sensitivity monoclonal antibody 3F10, which will be described in detail in the following Examples, as the anti-glycated hemoglobin antibody.

In the method according to the third embodiment of the present invention, a solution containing a monoclonal antibody specific for human glycated hemoglobin is mixed with a sample. Since the turbidity of the mixture increases when the sample contains glycated hemoglobin, glycated hemoglobin in the sample can be detected by measuring the change in the turbidity of the mixture. Also in this case, it is preferable to use the high sensitive monoclonal antibody 3F10, which will be described in detail in the following Examples, as the monoclonal antibody specific for human glycated hemoglobin.

As unsensitized latex particles to be employed in the methods according the fourth and fifth embodiment of the present invention, any commercially available latex particles including ones mentioned above may be used as it is or preferably after washing it several times with a Tris-succinic acid, phosphate or acetate buffer.

Binding of the anti-glycated hemoglobin antibody to particles in the method according to the fifth embodiment of the present invention may generally be effected by a physical adsorption method. That is, the particles are mixed with the antibody diluted to a level of 1 to 50 μg/ml so as to give a concentration of the particles of 0.1 to 10 % (w/v), and the mixture is stirred at a temperature in the range of from 4° C. to room temperature. After thoroughly washing by means of centrifugation, the resulting product is stored in a 1% by weight BSA solution until its use.

The unsensitized latex particles to be used in the method of the present invention have a particle size of from 0.05 to 5 μm, preferably from 0.1 to 2 μm, which are used by dispersing in a usually used buffer solution.

The unsensitized latex particles, a sample and the anti-glycated hemoglobin anti,body are mixed at a temperature ranging from 4° C. to 40° C., and the agglutinations are formed immediately after the mixing.

The glycated hemoglobin in a sample can be detected by mixing the sample with the anti-glycated hemoglobin antibody and the particles on, for example, a black slide glass and then observing the presence of agglutinated and precipitated particles. The glycated hemoglobin can also be determined quantitatively by an absorption measurement. In that case, the particles may preferably have a small particle size, but the change in the absorbance are measurable even with particles of about 1 μm in size if blank can be removed. In addition, glycated hemoglobin in a sample can be detected more quickly with more higher sensitivity by the use of unsensitized latex particles and latex particles to which the anti-glycated hemoglobin antibody is bound.

Agglutination of the latex particles can also be confirmed in the following manner. When latex particles having a larger particle size of 0.05 to 5 μm are used, their agglutination can be observed with the naked eye. When latex particles having a smaller size of 0.05 to 1.0 μm are used, their agglutination can be confirmed by spectrometrically measuring scattered light at a wave length of from 400 to 800 nm or using infrared light. In this way, glycated hemoglobin in a sample can be detected. Also in this case, it is preferable to use the high sensitive monoclonal antibody 3F10 described in the following Examples as the monoclonal antibody specific for human glycated hemoglobin.

The following examples are provided to further illustrate the present invention. It is to be understood, however, that the examples are for purpose of illustration only and are not intended as a definition of the limits of the present invention.

EXAMPLE 1

(1) Preparation of monoclonal antibody specific for glycated hemoglobin:

Glycated hemoglobin was thoroughly dispersed in Freund's complete adjuvant, and mice of Balb/c line were immunized with 100 µl of the suspension four times at intervals of two weeks. The spleen was excised from each of the immunized mice to obtain $10^6$ spleen cells which were subsequently fused with mouse myeloma cells in the presence of PEG. After culturing the fused cells, the resulting culture supernatant was checked for the presence of an anti-human glycated hemoglobin antibody by ELISA method. Thereafter, positive cells for the antibody were checked by the limiting dilution method to isolate anti-human glycated hemoglobin antibody-producing cells.

The thus obtained cells were used as anti-human glycated hemoglobin mouse monoclonal antibody-producing cells (hybridoma cells) and cultured in a large scale, and the cultured cells were administered to mice by intraperitoneal injection. After 2 weeks of the administration, the ascitic fluid was collected at intervals of 3 days to obtain the anti-human glycated hemoglobin monoclonal antibody of interest. The thus obtained anti-human glycated hemoglobin monoclonal antibody was named 3F10, and a hybridoma capable of producing 3F10 has been deposited at National Institute of Bioscience and Human-Technology, Agency of Industrial Science and Technology, Ministry of International Trade and Industry of Japan under accession No. FERM P-12998 (FERM BP-4311 under the Budapest Treaty). It was confirmed that the monoclonal antibody 3F10 is IgG.

(2) Measurement of human glycated hemoglobin by ELISA:

A 10 µg/ml solution of an anti-human hemoglobin antibody (rabbit antibody) was dispensed in 50 µl portions into wells of a 96 well plate for ELISA use (available from Nunc) and allowed to stand overnight at 4° C. The resulting plate was washed five times with a phosphate-buffered physiological saline containing 2% by weight BSA and 0.02% by weight Tween 20 and then stored at 4° C. after distributing the same buffer in 200 µl portions. After removing the supernatant fluid, 150 µl of a sample containing glycated hemoglobin was added dropwise to each well of the plate and allowed to stand for 2 hours at room temperature. The thus treated plate was then washed four times with physiological saline containing 0.02% by weight Tween 20.

Next, a peroxidase-labeled anti-human glycated hemoglobin-specific mouse monoclonal antibody solution (500 ng/ml) was distributed in 150 µl portions into wells of the above plate and allowed to stand for 2 hours at room temperature. After washing the plate four times with the physiological saline containing 0.02% by weight Tween 20, a 0.05% by weight $H_2O_2$ solution containing 0.1% by weight ABTS (2,2'-azobis(3-ethylbenzothiazoline-6-sulfonic acid)) was distributed in 200 µl portions into wells of the thus washed plate and allowed to stand for 30 minutes at room temperature to effect color development. Thereafter, the thus developed color was measured colorimetrically by measuring absorbances at 415 nm and 492 nm. The results are shown in Table 1.

TABLE 1

| Ratio of glycated hemoglobin to total hemoglobin (%) | Ratio of Absorbance at 415 to Absorbance at 492 |
| --- | --- |
| 0 | 0.06 |
| 1 | 0.10 |
| 3 | 0.18 |
| 6 | 0.29 |
| 9 | 0.47 |
| 12 | 0.61 |
| 15 | 0.80 |
| 18 | 1.00 |

EXAMPLE 2 AND COMPARATIVE EXAMPLE 1

Using the anti-glycated human hemoglobin monoclonal antibody prepared in Example 1 and a commercially available anti-human glycated hemoglobin monoclonal antibody, glycated human hemoglobin contained in samples in varied amounts of was quantitatively determined in the following manner.

The anti-glycated human hemoglobin monoclonal antibody prepared in Example 1 or a commercially available anti-human glycated hemoglobin monoclonal antibody (Chemicon International Inc. (U.S.A.)) was subjected to sensitization onto a 96 well microplate. To the resulting microplate was added peroxidase (POD)-labeled glycated hemoglobin antigen by varying the added amount (concentration). After carrying out the immune reaction at room temperature for 2 hours, the plate was washed with PBS-Tween. Thereafter, ABTS/$H_2O_2$ (substrate) was distributed in 100 µl portions into wells of the thus treated plate, and the reaction was proceeded out at room temperature for 1 hour. After adding 50 µl of a reaction termination solution, absorbance at a wave length of 415 nm was measured, with the results shown in FIG. 1.

As is evident from FIG. 1, the commercially available anti-human glycated hemoglobin antibody can hardly respond to the increasing amount of the antigen (Comparative Example 1), while the absorbance increases in proportion to the amount of the antigen when the anti-glycated human hemoglobin monoclonal antibody prepared in Example 1 is used (Example 2). In consequence, it was confirmed that glycated hemoglobin can be measured over a broad range of concentration by the use of the anti-glycated human hemoglobin monoclonal antibody prepared in Example 1.

EXAMPLE 3

A 2 ml portion of Tris-succinic acid buffer (pH 5.5) containing 0.025% of unsensitized polystyrene latex particles of 0.254 µm (available from Japan Synthetic Rubber Co., Ltd.) was added to a cell of which the temperature was controlled to at 37° C. An antigen solution containing 1 mg/ml of hemoglobin purified by means of a ion-exchange chromatography was added thereto, and the resulting mixture was stirred for 5 minutes at 37° C. After the completion of the stirring, 2 µl portion of an antibody solution containing 8 mg/ml of the anti-glycated hemoglobin monoclonal antibody prepared in Example 1 was added thereto to give a final concentration of the antibody of 8 µg/ml. From immediately thereafter, change of the absorbance with the passage of time was observed by the measurement of the absorbance at 750 nm by Hitachi 220 spectrophotometer. During the measurement of the absorbance, a commercially available anti-human hemoglobin antibody (Chemicon International Inc. (U.S.A.)) was further added to the cell so as to give the same final concentration of the previously added antibody (8 µg/ml).

The same procedure was repeated to observe change of the absorbance with the passage of time, except for that glycated hemoglobin was used in place of the hemoglobin, the anti-glycated hemoglobin monoclonal antibody was used in place of the anti-hemoglobin antibody, and the anti-hemoglobin antibody was used in place of the anti-glycated hemoglobin monoclonal antibody.

Figure 2:
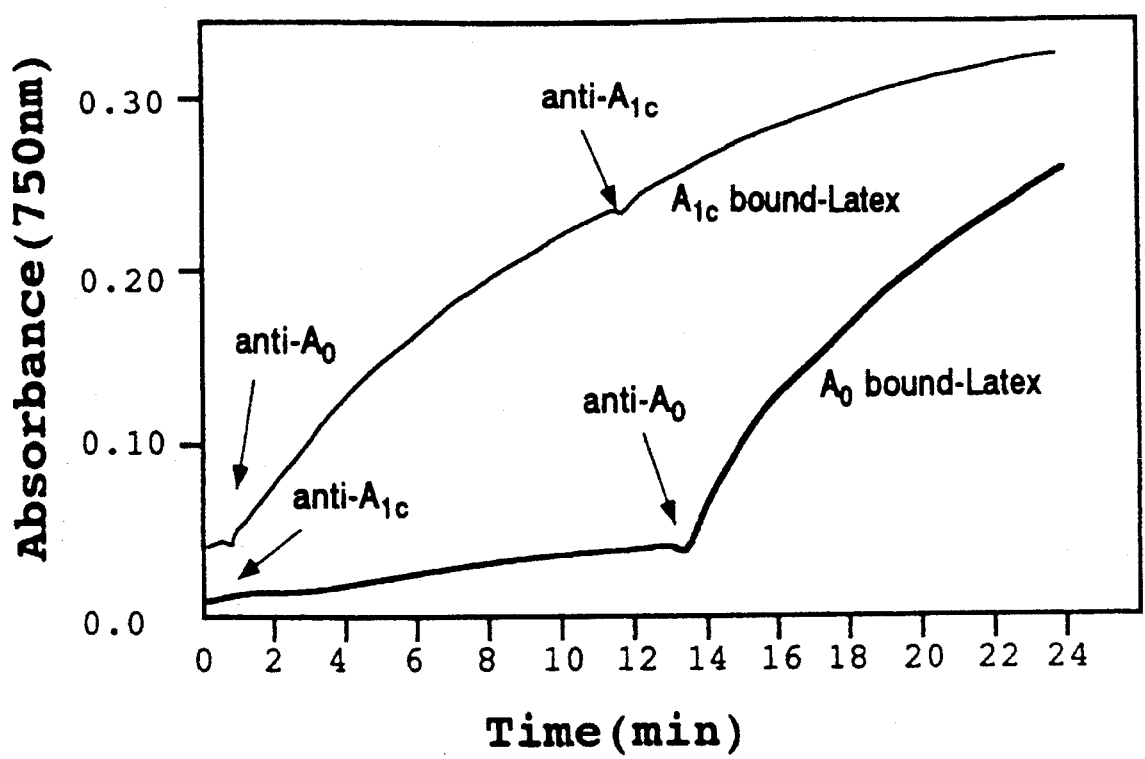
FIG. 2 is a graph showing the specificity of the anti-glycated hemoglobin monoclonal antibody prepared in Example 1 for glycated hemoglobin.

The results are shown in FIG. 2.

As the results shown in FIG. 2 indicate, the anti-glycated hemoglobin monoclonal antibody (anti-$A_{1c}$) prepared in Example 1 did not substantially react with the hemoglobin-bound latex particles ($A_O$-bound latex), but agglutination reaction began to proceed when the anti-hemoglobin antibody (anti-$A_O$) was added, thereby increase in the absorbance occurred. On the other hand, in the case where the glycated hemoglobin-bound latex particles ($A_{1c}$-bound latex) were used, the anti-glycated hemoglobin monoclonal antibody and the anti-human hemoglobin antibody showed the equivalent reactivity.

Accordingly, it was confirmed that the anti-glycated hemoglobin monoclonal antibody prepared in Example 1 possesses a superior specificity to glycated hemoglobin.

EXAMPLE 4
Preparation of anti-glycated hemoglobin mouse monoclonal antibody-bound latex particle:

A 100 µl portion of a solution containing 10% by w/v of the same latex particles of 0.254 µm in particle size as used in Example 3 was added to 900 µl of 20 mM acetate buffer (pH 6.0) containing 40 µg/ml of the anti-human glycated hemoglobin monoclonal antibody 3F10 obtained in Example 1. After stirring the mixture using an end-over mixer, the antibody-bound latex particles were recovered by centrifugation (5,000 g×15 minutes), washed four times with physiological saline and then suspended in 20 mM acetate buffer (pH 5.0) containing 1% by weight of BSA so as to give the concentration of 0.5% by weight, and then stored.

EXAMPLE 5
Measurement of human glycated hemoglobin by latex agglutination:

A 5 µl portion of a human erythrocyte extract (pH 5.0) was mixed with 50 µl of the latex suspension prepared in Example 3 on a black slide glass, and the mixture was gently waved several times. One minute thereafter, presence of the resulting agglutination was observed with the naked eye. The results are shown in Table 2.

TABLE 2

| Ratio of glycated hemoglobin to total hemoglobin (%) | Agglutination |
| --- | --- |
| 0 | − |
| 2 | − |
| 4 | − |
| 6 | + |
| 8 | + |
| 16 | + |

EXAMPLE 6
Measurement of changes in absorbance by latex agglutination:

A 2 ml portion of a 0.025% by weight suspension of anti-glycated hemoglobin mouse monoclonal antibody 3F10-bound latex particles having a particle size of 0.254 µm, which has been prepared in the manner as in Example 3, was mixed in a cell with 5 µl of each of three hemolytic samples. (Samples A, B and C), and periodical changes in the absorbance at a wave length of 750 nm were examined. Results of the measurement are shown in Table 3.

TABLE 3

| Time (second) | Absorbance | | |
| --- | --- | --- | --- |
| | Sample A | Sample B | Sample C |
| 0 | 0.700 | 0.711 | 0.731 |
| 30 | 0.721 | 0.762 | 0.842 |
| 60 | 0.740 | 0.812 | 0.955 |
| 90 | 0.760 | 0.863 | 1.051 |
| 120 | 0.770 | 0.912 | — |

EXAMPLE 7

A 2 ml portion of a solution containing 0.025% by weight of unsensitized polystyrene latex particles having a particle size of 0.254 µm was mixed with 5 µl of a hemolytic sample. After 5 minutes of the mixing, 50 µg of the anti-glycated hemoglobin mouse monoclonal antibody 3F10 obtained in Example 1 was added to the mixture and immediately applied to Hitachi 220 spectrophotometer to measure the change in the absorption at a wave length of 750 nm while stirring at 37° C. Results of the measurement of 5 samples are shown in Table 4.

TABLE 4

| Time (second) | Changes in absorbance at 750 nm | | | | |
| --- | --- | --- | --- | --- | --- |
| | Sample D | Sample E | Sample F | Sample G | Sample H |
| 0 | 0.721 | 0.741 | 0.736 | 0.730 | 0.751 |
| 30 | 0.752 | 0.705 | 0.784 | 0.725 | 0.861 |
| 60 | 0.780 | 0.701 | 0.833 | 0.730 | 0.970 |
| 90 | 0.805 | 0.720 | 0.880 | 0.740 | 1.070 |
| 120 | 0.829 | 0.733 | 0.933 | 0.751 | 1.170 |
| 180 | 0.855 | 0.745 | 0.991 | 0.763 | — |

EXAMPLE 8
Preparation of anti-glycated hemoglobin mouse monoclonal antibody-bound latex particle:

A 100 µl portion of a solution containing 10% by w/v of latex particles of 2 µm in particle size was added to 900 µl of 20 mM acetate buffer (pH 6.0) containing 40 µg/ml of the anti-human glycated hemoglobin monoclonal antibody 3F10 obtained in Example 1. After stirring the mixture using an endo-over mixer, the antibody-bound latex particles were recovered by centrifugation (5,000 g×15 minutes), washed four times with physiological saline and then suspended in 20 mM acetate buffer (pH 5.0) containing 1% by weight of BSA so as to give the concentration of 0.5% by weight, and then stored.

A 5 µl portion of a sample was mixed with 100 µl of a solution containing 0.025% by weight of unsensitized polystyrene latex particles of 0.05 µm in particle size and then with 1 ml of the thus prepared anti-glycated hemoglobin mouse monoclonal antibody-bound latex particle dispersion, and the mixture was immediately checked for the increase in the absorbance at 800 nm while stirring. Table 5 shows relationship between ratios (%) of glycated hemoglobin to total hemoglobin in a sample and changes in the absorbance per minute.

TABLE 5

| Ratio of glycated hemoglobin to total hemoglobin (%) | Changes in absorbance per minute |
| --- | --- |
| 0 | 0.01 |
| 2 | 0.12 |
| 4 | 0.24 |
| 6 | 0.35 |
| 8 | 0.42 |

Thus, it is apparent that there has been provided, in accordance with the present invention, a simple and quick measuring method of glycated hemoglobin.

While the invention has been described in detail and with reference to specific examples thereof, it will be apparent to one skilled in the art that various changes and modifications can be made therein without departing from the spirit and scope thereof.

What is claimed is:

1. A method of measuring hemoglobin $A_{1c}$ which comprises:

mixing a sample with unsensitized latex particles and an anti-hemoglobin $A_{1c}$ antibody specific for native glycated hemoglobin to cause an immunoagglutination reaction, and then measuring agglutinations formed by the immunoagglutination reaction.

2. The method of claim 1, wherein said unsensitized latex particles have a particle size of from 0.05 to 5 μm.

* * * * *